United States Patent [19]

Chabardes et al.

[11] Patent Number: 5,177,265
[45] Date of Patent: Jan. 5, 1993

[54] PROCESS FOR THE PREPARATION OF CITRAL

[75] Inventors: Pierre Chabardes, Sainte Foy Les Lyon; Jacques Chazal, Saint-Fons, both of France

[73] Assignee: Rhone-Poulenc Sante, Cedex, France

[21] Appl. No.: 743,358

[22] PCT Filed: Dec. 28, 1990

[86] PCT No.: PCT/FR90/00958
§ 371 Date: Oct. 31, 1991
§ 102(e) Date: Oct. 31, 1991

[87] PCT Pub. No.: WO91/09830
PCT Pub. Date: Jul. 11, 1991

[30] Foreign Application Priority Data

Jan. 3, 1990 [FR] France ............... 90 00018

[51] Int. Cl.$^5$ ............... C07C 45/00; C07C 47/21
[52] U.S. Cl. ............... 568/460; 568/458; 568/459
[58] Field of Search ............... 568/460, 486, 459

[56] References Cited

U.S. PATENT DOCUMENTS

| 3,965,193 | 6/1976 | Goetz et al. | 568/460 |
| 4,021,411 | 5/1977 | Goetz et al. | 568/460 |
| 4,209,644 | 6/1980 | Ichikawa et al. | 568/596 |
| 4,288,636 | 9/1981 | Nissen et al. | 568/460 |
| 4,933,500 | 6/1981 | Chabardes et al. | 568/460 |
| 4,933,550 | 6/1990 | Chabardes et al. | 568/460 |

FOREIGN PATENT DOCUMENTS

| 0681790 | 3/1964 | Canada | 568/465 |
| 2305629 | 8/1974 | Fed. Rep. of Germany | 568/460 |
| 2160525 | 6/1973 | France | 568/460 |
| 2353512 | 12/1977 | France | 568/460 |
| 0344043 | 11/1988 | France | 568/460 |
| 592035 | 10/1977 | Switzerland | 568/460 |

*Primary Examiner*—Werren B. Lone
*Attorney, Agent, or Firm*—Finnegan, Henderson, Farabow, Garrett and Dunner

[57] ABSTRACT

An improved method for preparing citral in liquid phase from prenol and prenal, wherein, in a single reaction enclosure, the prenol and prenal are condensed in the presence of a mineral acid at a concentration of about $5.10^{-3}$ mole for one mole of prenal, 90 to 95% of the acid is neutralized, and once excess prenal and prenol is eliminated, the citral is distilled.

5 Claims, No Drawings

PROCESS FOR THE PREPARATION OF CITRAL

The present invention relates to a process for the preparation of citral starting from prenol and prenal.

It relates more particularly to an improved process for the preparation of citral starting from prenol and prenal.

It is known, according to French Patent No. 72.40678 published under the number 2,160,525, to prepare $\alpha,\beta$-ethylenically-linked aldehydes by reaction at elevated temperature in liquid phase of an $\alpha,\beta$-ethylenically-linked aldehyde and an allylic alcohol. The $\alpha,\beta$ethylenically-linked [sic] aldehyde can be 3,3-dimethylacrolein, known under the name prenal, and the ethylenic alcohol can be 3-methyl-2-buten-1-ol known under the designation prenol.

The condensation reaction is preferably carried out in the presence of an acid catalyst at temperatures between 100° and 250° C. The acid used as a catalyst is chosen from amongst the inorganic acids such as sulphuric acids, phosphoric acids, halogenated acids, nitric acid, sulphurous acid, phosphorous acid, perchloric acid, boric acid, silicic acid, acid salts with dissociable hydrogen and heterogeneous acids. Organic acids can also be used. The quantity of acid used, if it is a mineral acid having a PK [sic] of 0 to approximately 3, is between 0.01 and 0.5% during the entire reaction, which can be divided into two reaction steps: formation of the acetal and decomposition of the latter by cracking.

It is additionally known according to U.S. Pat. No. 4,288,636 to prepare citral by heating a diprenylic acetal in the presence of an inert liquid having a boiling point higher than prenol and lower than citral at the reaction pressure. The inert liquid is preferably 3,3,7-trimethyl-4-oxaocta-1,6-diene.

The quantity of phosphoric acid used is between 0.001 and 0.5% by weight and preferably between 0.005 and 0.05% by weight.

It is likewise known according to the Patent FR 2,353,512 to prepare the acetals by condensation of an aldehyde with an alcohol in the presence of a distillable acid which is preferably nitric acid. In this case, the quantity of acid used varies between $10^{-6}\%$ and 1% by weight with respect to the starting compounds and preferably between $10^{-4}$ and $10^{-2}\%$. It is even specified in this text that when a less strong acid is used, for example phosphoric acid, the quantity of acid can extend to 10%, that is to say is multiplied by ten with respect to nitric acid.

Nothing indicates, even on gathering together these three documents, of which certain and particularly the third have very high areas of concentration, that the concentrations of acid may be different in the two steps: acetalisation and cracking, since the concentration ranges indicated have a certain area of overlap.

In comparing these three texts, it even seems that the acidity necessary for acetalisation would be less than or equal to the acidity necessary for cracking.

In employing these processes at the laboratory level, it was apparent to us that the acidity necessary for the formation of the acetal and the acidity necessary for the cracking step were different and that the yield was improved on carefully controlling the acidity of the reaction medium during the process.

The present invention therefore relates to an improved process for the preparation of citral starting from prenol and prenal, characterised in that, in the same reaction space:

in a first step, the condensation of prenol with prenal is carried out in the presence of a mineral acid at a concentration of approximately $5 \times 10^{-3}$ mol per mole of prenal introduced and of a solvent forming an azeotrope with water, in a second step, 90% to 95% of the acidity is neutralised, and in a third step, the reaction medium is heated, the prenol and the prenal are removed and recycled to the first step, then the citral is distilled off.

The use of a very weak acidity during the cracking step allows the yields of citral to be increased.

Thus, when in the cracking step a concentration of acid of $10^{-3}$ mol per mole of acetal is used (corresponding to 1 mol of starting prenal), citral is not obtained (Example 2). On the other hand, when in the acetalisation step a concentration of acid of $10^{-4}$ mol per mole of prenal is used, the acetalisation yield reaches 30% at the maximum (Example 3).

It was not obvious from reading the patents cited above to conclude that the acetalisation reaction should be carried out with a concentration of acid five to ten times larger than the cracking reaction in order that the process can be employed in an economically profitable manner.

The acid used is preferably phosphoric acid.

The molar ratio of prenol calculated with respect to prenal is preferably between 2 and 2.5.

The solvent forming an azeotrope with water is preferably toluene.

It may also be advantageous to add traces of hydroquinone.

The acetalisation reaction is preferably carried out at a temperature between 60° and 90° C. under a pressure between 8 and $14 \times 10^3$ pascals (6 to 10 cm of mercury).

The toluene is distilled off with the water formed during the reaction.

The neutralisation of the acidity is carried out by means of a base chosen from amongst the alkali metal salts of acetic acid, preferably potassium acetate or sodium acetate, as well as amongst the acid carbonates of sodium or of potassium or the hydroxides of alkali metals.

Between 90% and 95% of the acid introduced is neutralised.

Cracking of the resultant acetal is then carried out on the crude reaction product without elimination of the secondary condensation products and without isolating diprenylic acetal but by liberating the excess of prenal and of prenol introduced at the start.

Cracking of the acetal is carried out at a temperature between 120° and 150° C. under a pressure between 8 and $16 \times 10^3$ pascals (6 and 12 cm of mercury). The prenol formed in the cracking reaction is eliminated first, then the medium is heated to a temperature of 120° C. to distil off the citral.

The present invention will be described more completely with the aid of the following examples which may not be considered in any case as limiting the invention.

EXAMPLE 1

Acetalisation

The following are introduced into a reactor:
35.1 g of 97.2% prenal (0.405 mol)

87.0 g of 100% prenol (1.010 mol)

10.0 g of toluene 2 ml of phosphoric acid in 0.98 molar solution containing 1.960 mmol of phosphoric acid.

A distillation column containing 5 theoretical plates is used. The reaction medium is heated to a temperature between 72° and 90° C. at a pressure of 80 mm of mercury for 6 hours. 8.5 ml of water are distilled off. After reaction, the toluene is distilled off in the course of a quarter of an hour. The vacuum is increased to 15 mm of mercury to remove the remainder of the toluene.

The rate of conversion of prenal, which is the ratio:

$$\frac{(\text{prenal introduced} - \text{prenal recovered})}{\text{prenal introduced}}$$

is 83%, and the yield of diprenylic acetal, which corresponds to the ratio:

$$\frac{(\text{diprenylic acetal formed})}{\text{prenal introduced}}$$

is 75.6%.

Neutralisation

The reaction medium is neutralised by adding 180 mg of potassium acetate and 100.5 mg of hydroquinone. The solution then contains $4 \times 10^{-4}$ mol of phosphoric acid.

A distillation under 15 mm of mercury is then carried out so as to recover the excess prenal and prenol (recovery 31.8 g).

Cracking

The reaction medium is then heated at 125° C.-140° C. under 90 mm of mercury for 3 hours 30 min. The prenol formed during the reaction and then the citral are distilled off allowing the temperature to rise to 120° C. and lowering the pressure to 0.05 mm of mercury. 45.8 g of distillate containing 38.9 g of citral are recovered, which represents a 63% yield with respect to prenal employed and 78% with respect to prenal converted.

EXAMPLE 2 (COMPARATIVE)

Acetalisation

The following are introduced:

33.6 g of 99.5% prenal (397 mmol)

86 g of 99.6% prenol (994 mmol)

200 μl of 85% phosphoric acid corresponding to (2.95 mmol): 0.17% by weight
: $7.4 \times 10^{-3}$ mol/mole of prenal After reaction under the same conditions as in Example 1, a reaction mixture of 111.9 g is obtained in which the prenol, prenal and resultant acetal are determined.

The rates of conversion are 77% for prenal and 64% for prenol. The yield of acetal is 74% with respect to the prenal added.

Neutralisation is not carried out, but it is checked by potentiometric determination that all the phosphoric acid initially added is present in the crude reaction mixture. Hydroquinone is added to this mixture which contains the acetal, hydroquinone and phosphoric acid in a molar ratio of $1:23 \times 10^{-4}:100 \times 10^{-4}$.

Cracking

Cracking is carried out under the same conditions as in Example 1 by heating to a temperature of 97° C. in order not to degrade the acetal but lowering the pressure to 15 mm of mercury. Traces of citral are not obtained but only polymers, high molecular weight products and ethers.

EXAMPLE 3 (COMPARATIVE)

Acetalisation

The following are introduced:

25.2 g of 99.5% prenal (298 mmol)

64.6 g of 99.6% prenol (747 mmol)

25.2 g of cyclohexane 140 mg of 0.98 m phosphoric acid (0.137 mmol), i.e. $4.6 \times 10^4$ mol per mole of prenal.

The mixture is heated to 110° C. at atmospheric pressure for 3 hours then at 250 mm of mercury for 2 hours.

The rate of conversion of the prenal is only 28%. On the other hand, the addition of acid to increase its concentration relative to the prenol to the same values as those used in the preceding examples allows the reaction to be monitored.

We claim:

1. A process for the preparation of citral starting from prenal and prenol, characterized in that,
    in the same reaction space,
    in a first step, the condensation of prenal with prenol is carried out in a liquid phase in the presence of a solvent forming an azeotrope with water and a mineral acid at a concentration of approximately $5 \times 10^{-3}$ mol per mole of prenal,
    in a second step, 90 to 95% of the mineral acid is neutralized and
    in a third step, after elimination of the prenal and prenol which have not reacted, the citral is distilled off.

2. The process of claim 1, characterized in that the solvent is toluene.

3. The process of claim 1, characterized in that the mineral acid is phosphoric acid.

4. The process of claim 1, characterized in that the neutralizing agent is an alkali metal acetate.

5. The process of claim 4, wherein the neutralizing agent is potassium acetate.

* * * * *